United States Patent
Giannantonio et al.

(10) Patent No.: US 7,154,087 B2
(45) Date of Patent: Dec. 26, 2006

(54) METHOD AND APPARATUS FOR CARRYING OUT ION MOBILITY SPECTROMETRY ANALYSES

(75) Inventors: Roberto Giannantonio, Oleggio (IT); Antonio Bonucci, Milan (IT); Luca Pusterla, Milan (IT); Gianluca Galliani, Milan (IT)

(73) Assignee: Saes Getters S.p.A., Lainate MI (IT)

( * ) Notice: Subject to any disclaimer, the term of this patent is extended or adjusted under 35 U.S.C. 154(b) by 0 days.

(21) Appl. No.: 11/040,351

(22) Filed: Jan. 21, 2005

(65) Prior Publication Data

US 2006/0054809 A1    Mar. 16, 2006

Related U.S. Application Data

(63) Continuation of application No. PCT/IT03/00430, filed on Jul. 10, 2003.

(30) Foreign Application Priority Data

Jul. 22, 2002   (IT)   ............................ MI2002A1616

(51) Int. Cl.
*B01D 59/44*   (2006.01)
*H01J 49/00*   (2006.01)

(52) U.S. Cl. ...................... 250/287; 250/287; 250/282
(58) Field of Classification Search ................ 250/287, 250/282
See application file for complete search history.

(56) References Cited

U.S. PATENT DOCUMENTS

| 4,362,941 | A |   | 12/1982 | Castleman et al. |
| 4,812,649 | A |   | 3/1989 | Nakagawa |
| 4,855,595 | A | * | 8/1989 | Blanchard .................... 250/287 |
| 5,294,794 | A | * | 3/1994 | Davies ........................ 250/287 |
| 5,457,316 | A |   | 10/1995 | Cohen et al. |
| 5,955,886 | A |   | 9/1999 | Cohen et al. |
| 6,107,624 | A |   | 8/2000 | Döring et al. |
| 6,229,143 | B1 |   | 5/2001 | Wernlund |

FOREIGN PATENT DOCUMENTS

| DE | 198 07 699 A1 | 9/1999 |
| EP | 0 026 683 A2 | 4/1981 |
| EP | 0 253 155 A1 | 1/1988 |
| EP | 0 316 514 A1 | 5/1989 |
| EP | 0 528 426 A1 | 2/1993 |

* cited by examiner

*Primary Examiner*—Nikita Wells
*Assistant Examiner*—Jennifer Yantorno
(74) *Attorney, Agent, or Firm*—Akin Gump Strauss Hauer & Feld, LLP (57) ABSTRACT

A method and apparatus for carrying out analyses of a gas comprising one or more species by using an ion mobility spectrometer which includes a plurality of electrodes arranged in a chamber divided by an electrifiable grid into a reaction zone provided with an inlet for the gas to be analyzed and a drift zone provided with at least one ion detector. The electrodes generate at least one electric field non-uniform in space along the longitudinal axis of the chamber.

21 Claims, 8 Drawing Sheets

METHOD AND APPARATUS FOR CARRYING OUT ION MOBILITY SPECTROMETRY ANALYSES

CROSS-REFERENCE TO RELATED APPLICATIONS

This application is a continuation of International Application No. PCT/IT03/00430, filed Jul. 10, 2003, which was published in the English language on Jan. 29, 2004, under International Publication No. WO 2004/010132 A1, and the disclosure of which is incorporated herein by reference.

BACKGROUND OF THE INVENTION

The present invention relates to a method for carrying out ion mobility spectrometry analyses, and in particular, to the simultaneous analysis of more impurities contained in very pure gases, such as those employed in the microelectronic industry. The present invention also relates to an instrument which carries out said method.

Ion mobility spectrometry is generally known in the field of chemical analyses with the abbreviation IMS, which also indicates the instrument for carrying out the analytic technique (in this case abbreviating the terms Ion Mobility Spectrometer).

The interest for the IMS technique comes from its extremely high sensitivity, associated with the reduced size and cost of the instrument. By operating in suitable conditions it is possible to detect species in gas or vapor phase in a gas mixture in picograms quantities (pg), i.e., $10^{-12}$ grams, or in part per trillion concentrations (ppt), i.e., equal to a molecule of analyzed substance per $10^{12}$ molecules of sample gas. The gas forming most of the gas mixture will be referred to hereinafter as "carrier gas", while the mixture itself will be referred to hereinafter as "sample gas."

There are many application fields of this technique, both in civilian sectors (in particular, for the detection in the industry of inorganic or organic contaminants in clean rooms or of noxious species in the industrial exhausts) and in military sectors (in particular, for the detection of the presence of explosive or toxic substances, such as nerve gases). IMS analysis methods and instruments are disclosed, for example, in U.S. Pat. No. 5,457,316 (Cohen, et al.); U.S. Pat. No. 5,955,886 (Cohen, et al.); and U.S. Pat. No. 6,229,143 (Wernlund).

A known IMS instrument is essentially made up of a cylindrical chamber having at one end the inlet for the sample gas, which is introduced through an inlet electrode and a ionizing member and at the opposite end a detector of charged particles. The detector is normally kept at the ground potential, while the inlet electrode is kept at a potential higher or lower than that of the detector (instrument working in the positive or negative mode, respectively). In the remainder of the description, for simplicity and clarity, reference will always be made to the use of an IMS instrument in the positive mode, which corresponds to the most common condition of use, but all these considerations are also valid for the use in negative mode. An electrifiable grid divides the chamber into two zones, referred to in the field as a "reaction zone" (on the inlet side of the instrument) and a "drift zone" (on the detector side of the instrument). A series of electrodes, generally annular, are arranged along the walls of the two zones and are set at a determined voltage, so as to create between the inlet electrode and the detector an electric field, which is uniform in the direction of the longitudinal axis of the chamber and transports the ions toward the particle detector. During their motion, the ions are slowed down by a gas which is usually counter-flowing with respect to the direction of ion motion. This gas is introduced from a duct at the chamber end comprising the detector and is expelled by an outlet at the opposite end. The counter-flowing gas, defined as "drift gas" in the field, is an ultra-pure gas which can be the same as the carrier gas or different.

The ionizing member is commonly a beta radiation source comprising $^{63}$Ni. According to the working mode, the ions with a charge opposite to the charge of the inlet electrode ER are neutralized on or near the inlet electrode ER, while the ions with a charge of the same sign as this electrode undergo a repulsion and are accelerated in the reaction zone. The first ionization produces essentially exclusively ions of the carrier gas, due to its concentration being higher by several orders of magnitude than that of the other species, generally present as traces. The primary ions corresponding to the carrier gas are called "reactant ions" in the field. In the reaction zone the charge of the reactant ions is distributed among the present species according to their electron or proton affinities, to their ionization potentials or to their electronegativity, according to reactions of the kind:

$$R^+ + S_i \rightarrow R + S_i^+ \quad \text{(I)}$$

where R+ represents a reactant ion, R a neutral molecule deriving from the neutralization of the reactant ion (that is, a carrier gas molecule), Si a molecule of the i-th species to be analyzed and $S_i^+$ the ion corresponding to Si. The ions $S_i^+$ often give rise to complex species due to the association with one or more neutral molecules, but for ease of notation and without losing generality, reference will always be made to simple ions hereinafter.

All these ions are transported by the electric field toward the electrifiable grid, generally made up of linear and parallel conducting members, in particular metallic wires. The grid members are grouped in two mutually alternated series, so that each member of one series has two members of the other series as the closest members. The two series of members of the grid are normally biased with potential values higher and lower, respectively, than the potential of the grid electrode. A transversal electric field generally stronger than the one along the longitudinal axis of the chamber in that point is thus created on the grid plane, so that the ions present in the reaction zone are accelerated toward the members of one of the two series constituting the grid and neutralized. In these conditions, the grid is "closed" and prevents the ions from passing toward the drift zone.

When the analysis is to be carried out, the two series of grid members are brought at the same potential of the grid electrode, thereby canceling the transversal field. In these conditions, the grid is "open" so that the ions can advance into the drift zone. The grid opening lasts generally some hundreds of microseconds, and during this time, a portion of the ions present in the reaction zone is transferred to the drift zone. In particular, the grid is crossed by a portion of the ions contained in a cylindrical volume in the reaction zone adjacent to the grid, the height of which is determined by the relation:

$$l_a = v_i \times t_a \quad \text{(II)}$$

where $l_a$ is the height of the cylindrical volume, $v_i$ is the motion speed of the ion $S_i^+$ and $t_a$ is the opening time of the grid. The initial or central instant of the grid opening time slot is commonly assumed as the "time zero", that is, the analysis start.

In the drift zone, the ions are transported toward the detector with a motion speed which is the resultant of the acceleration due to the presence of the axial electric field and the deceleration due to the collisions with the drift gas. In particular, the motion speed of the i-th ion depends linearly on the electric field and is directly proportional to the temperature T and inversely proportional to the pressure P, according to the effect that the latter two terms have on the viscosity of the drift gas. While the acceleration due to the electric field acts to the same extent on the ions having the same charge (but in the IMS all the ions generally have a unitary charge), the deceleration acts in a different way on the ions according to the different size, shape and mass of the same, so that each ion has a characteristic motion speed and therefore a crossing time of the drift zone (defined as "drift time" in the field) generally different from that of the other ions. By recording the charges collected on the detector a spectrum is obtained comprising ion current peaks as a function of the time elapsed from the test start. The intensity of each peak in the spectrum is proportional to the amount of charge $C_{Si}^+$ transported by the ion $S_i^+$ which caused the peak.

Through calibrating tests in which sample gases containing a single species $S_i$ are analyzed, it is possible to obtain data such as speed and drift time of the ionic species $S_i^+$ in a given gas and at given temperature and pressure conditions, as well as the efficiency of the reaction I for that species. In ideal conditions and operating in the same conditions of the calibrating tests, this data could be employed in an IMS analysis for determining the presence of the species $S_i$ in the gas under exam according to the position of the peaks in the spectrum, and its concentration according to the relative size of the different peaks.

However, in a real analyses, the situation is much more complex, due to a number of phenomena which affect the above theoretical conditions.

A first phenomenon includes the possible presence of unexpected and unknown species $U_i$ (i=1, ..., m), for which calibration data are not available. These species may interfere with the analysis by subtracting charge from the ions $S_i^+$ or from ions $R^+$ according to reactions of the kind:

$$S_i^+ + U_i \rightarrow S_i + U_i^+ \qquad (III)$$

The result is a spectrum in which the peaks relating to the ions $S_i^+$ and the peak relating to the ion $R^+$ (defined in the field "reactant ion peak" and with the abbreviation RIP, which will be adopted in the following) have an intensity lower than in theoretical conditions or may even disappear, while there are peaks which cannot have an attribution.

Furthermore, the species formed in the reaction zone may react with other neutral species, already in the reaction zone or in the drift zone, with reactions of the kind:

$$S_i^+ + S_j \rightarrow S_i + S_j^+ \qquad (IV)$$

or $$S_i^+ + S_i \rightarrow (S_i)_2^+ \qquad (V)$$

Each reaction proceeds to different degrees and with different speeds according to the different kinetics and equilibrium constants for each reaction. These reactions cause the modification of the concentrations of the ions reaching the detector of the IMS instrument with respect to the concentrations initially formed by the direct reaction with the $R^+$ ions, so that the ions corresponding to a species could completely disappear and the latter cannot be detected anymore in the analysis. Reference can be made to the book "Ion Mobility Spectrometry", edited by G. A. Eiceman and Z. Karpas, published in 1994 by CRC Press, for a presentation of the complex charge transfer principles involved in these reactions.

Another problem of the IMS analyses is a rather limited range of concentrations of species $S_i$ that can be read by the instrument. IMS analyses require that the ion $R^+$ is not completely consumed in charge transfer reactions. If a species $S_i$ is present in too high a quantity, the reaction of type I continues until the ion $R^+$ is consumed. After the exhaustion of the primary reagent in the charge transfer, a concentration increase of $S_i$ does not correspond to a concentration increase of the ion $S_i^+$, so that the reading capability of the instrument is saturated and its upper reading threshold is reached. Besides, the whole quantitative IMS analysis is based on the determination of the area of the RIP, so that when the latter disappears from the spectrum (upon complete consumption of $R^+$), the determination of the impurities concentration in multi-component analyses becomes impossible. Due to the very high sensitivity of the technique, saturation is generally reached already with low concentrations of some species. For example, in the case of water, the maximum value in the read range of the instrument is of a few tens of parts per billion (ppb), so that the application field is limited to the analysis of gases with low impurity contents. This particular problem may be solved by mixing at known ratios the sample gas with an ultra-pure gas corresponding to the carrier gas, so as to dilute the concentration of the species $S_i$ and bring it back in the read range of the instrument. However, this makes the equipment more complex and expensive, since it requires the use of gas purifiers, calibration instruments for different gas flows and additional components compatible with the ultra-pure gases. Obviously, the instrument has also a lower read limit, even if very low, that is a concentration of a species $S_i$ under which the area of the corresponding peak is too low and the presence of the species cannot be determined anymore. Thus, there is a general problem of the read thresholds, both lower and upper, of the IMS instrument.

Furthermore, gases like $O_2$, CO, $H_2$, $H_2O$, etc., coming for instance from previous analyses, can be present on the inner surfaces of the instrument (such as the inner walls of the chamber, electrodes, etc.), either chemisorbed or physically adsorbed. Alternatively, these gases can be dissolved in the materials constituting the instrument. For example, steel, which the chamber is generally made of, normally contains hydrogen. These gases are released both in the reaction zone and in the drift zone. During the analysis, they form additional species $B_i$ (i=1, ..., r) which come into reactions of type I, III or IV. When these reactions occur in the reaction zone, a charge is removed from the species initially present in the sample gas and spurious peaks appear in the final spectrum. The same reactions, when they occur in the drift zone, may instead lead to spectrum distortions. Unlike the ions of the species $S_i$, which come into the drift zone all at the same time and start from the same position (the grid), the ions corresponding to these species are formed at different points of the drift zone, and therefore, reach the detector at different times according to the generation point. The consequence is that between the spectrum peaks the instrument reading is not zero, as it should be in theory, but there is instead a non-null spectrum "background" which complicates the determination of the area of the peaks or may make it practically impossible in the case of peaks with a lower intensity. The presence of the species $B_i$ also involves other drawbacks. First, these may react with species $S_i^+$ through reactions of type III or IV in the drift zone, thus causing an undesired attenuation of the charge quantity transferred by the species $S_i^+$ to the detector and a consequent reduction of the instrument sensitivity. Second, the interaction of species $B_i$ with the species $R^+$ in the drift zone may cause an undesired attenuation of the RIP, with a consequent reduction of the upper reading threshold of the instrument.

As a consequence, in IMS analyses, in particular multi-component quantitative analyses, there is a general problem of deviation from ideality, that gives rise through various mechanisms to distortions of the final spectrum, and thus to uncertainty and errors in the results obtained from these analyses.

BRIEF SUMMARY OF THE INVENTION

Briefly stated, the present invention comprises a method for carrying out analyses of a gas having one or more species by using an ion mobility spectrometer. The ion mobility spectrometer includes a plurality of electrodes arranged in a chamber divided by an electrifiable grid into a reaction zone provided with an inlet for the gas to be analyzed and a drift zone provided with at least one ion detector. The method includes the electrodes generating an electric field in the drift zone which has an intensity different from the electric generated in the reaction zone. The electric fields are uniform in a space along the longitudinal axis of the chamber in each of the reaction and the drift zones.

The present invention also comprises an instrument that carries out ion mobility spectrometric analyses of a gas comprising one or more species. The instrument includes a plurality of electrodes and at least one control circuit. The plurality of electrodes are arranged in a chamber divided by an electrifiable grid into a reaction zone provided with an inlet for the gas to be analyzed and a drift zone provided with at least one ion detector. The at least one control circuit varies the potential of the electrodes so as to generate an electric field that is non-uniform along an axis which crosses the chamber. The control circuit is configured to set the electrodes in the reaction zone and the electrodes in the drift zone at potentials generating two uniform electric fields with different intensities inside the reaction and drift zones along the longitudinal axis of the chamber.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
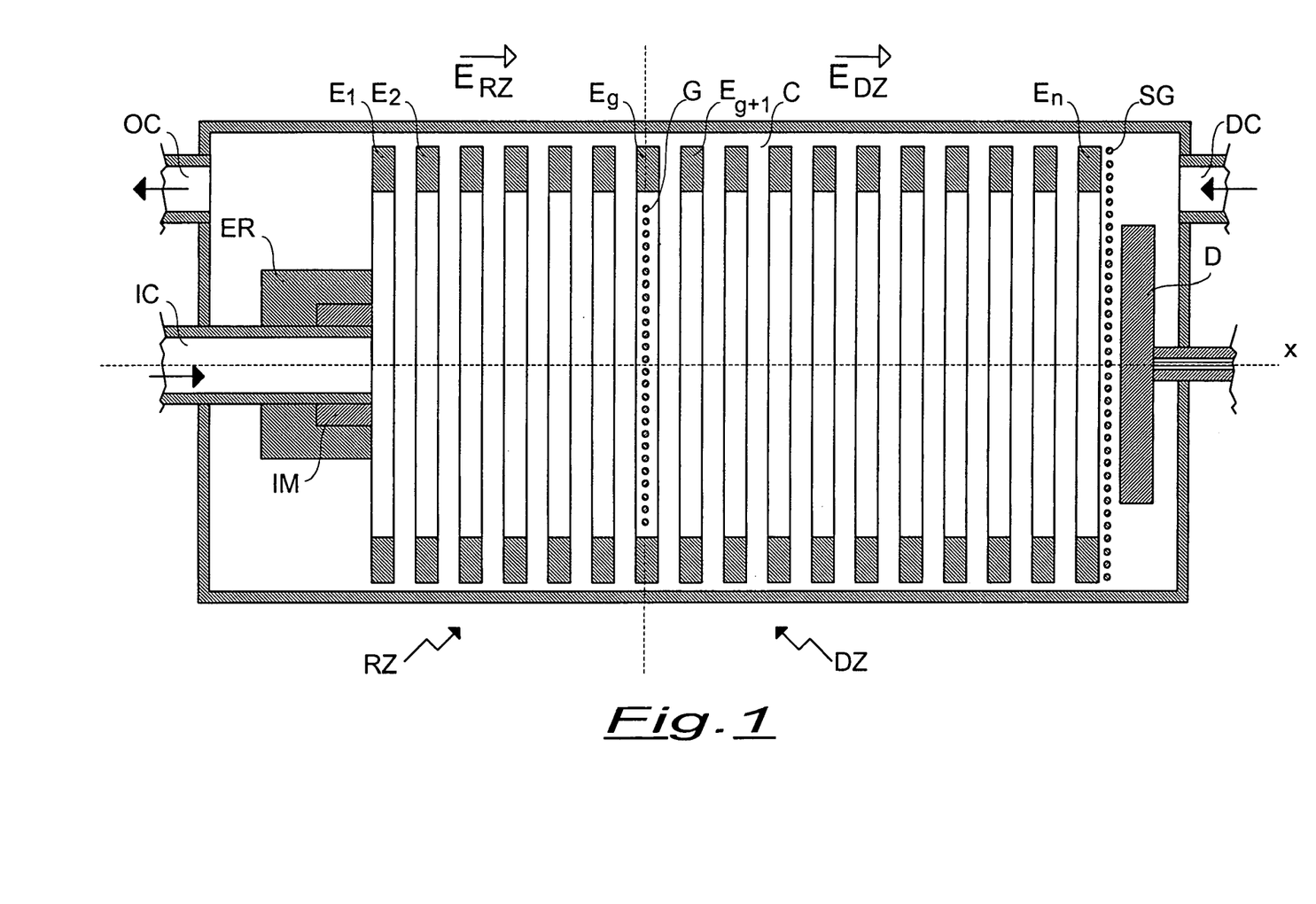
FIG. 1 is a longitudinal cross-section view of the chamber of the IMS instrument according to an embodiment of the invention.

Referring to FIG. 1, it is seen that the IMS instrument according to the present embodiment of the invention comprises, in a known way, a chamber C having a substantially cylindrical shape. One end of chamber C is provided with an inlet IC for the sample gas, around which a ionizing member IM and more externally an inlet electrode ER are arranged, while the opposite end of chamber C is provided with a detector D for charged particles. Detector D is normally kept at the ground voltage, while the inlet electrode ER is kept at a voltage greater or lower than that of detector D. An electrifiable grid G divides chamber C into a reaction zone RZ comprising inlet IC and a drift zone DZ comprising detector D. In the present embodiment, grid G comprises two alternated series of conductive wires parallel to each other, which are arranged perpendicularly to the longitudinal axis of chamber C. A series of electrodes $E_i$ (i=1, . . . , n) is arranged along the walls of the two zones RZ and DZ. These electrodes $E_i$ have a substantially annular shape each one is set at a suitable voltage, so as to create between the inlet electrode ER and detector D at least one electric field in the direction of the longitudinal axis x of chamber C. A screen grid SG is arranged between the last electrode $E_n$ and detector D to avoid the creation on the latter of an "image charge," i.e., the build up of an electrostatically induced charge on detector D. The wires of grid G are inserted into the central cavity of an electrode $E_g$. The wires of grid G are however electrically insulated from the electrode $E_g$. This electrode $E_g$, called grid electrode, is the last electrode of the electrode series $E_1, E_2, \ldots, E_g$ comprised within the reaction zone RZ and is also the first electrode of the series of electrodes $E_g, E_{g+1}, \ldots, E_n$ comprised within the drift zone DZ. During their motion, the ions are preferably slowed down by a drift gas which is introduced through an inlet DC arranged at the end of chamber C where detector D is present, and which flows out through an outlet OC at the other end of chamber C.

The IMS instrument according to the present embodiment of the invention can therefore be similar, in its geometric construction, to the known IMS instruments. But, while in known IMS instruments the circuit controlling the voltage of electrodes $E_i$ can only produce a uniform electric field along the longitudinal axis x of chamber C from electrode ER to detector D, the instrument according to the present invention is provided with a control circuit capable of producing a non-uniform electric field along the longitudinal axis X. In particular, the control circuit is suitable for controlling in an independent manner the potential of the electrodes $E_1$, $E_2, \ldots, E_g$ arranged in the reaction zone RZ and the potential of the electrodes $E_g, E_{g+1}, \ldots, E_n$ arranged in the drift zone DZ. With this arrangement, electrodes $E_1, E_2, \ldots, E_g$ and electrodes $E_g, E_{g+1}, \ldots, E_n$ can generate at least two different electric fields in the reaction zone RZ and in the drift zone DZ (referred to hereinafter as $E_{RZ}$ and $E_{DZ}$, respectively). In a preferred embodiment, for simplifying the control circuit, the electric fields $E_{RZ}$ and $E_{DZ}$ are uniform within the relevant zones RZ and DZ.

Figure 2:
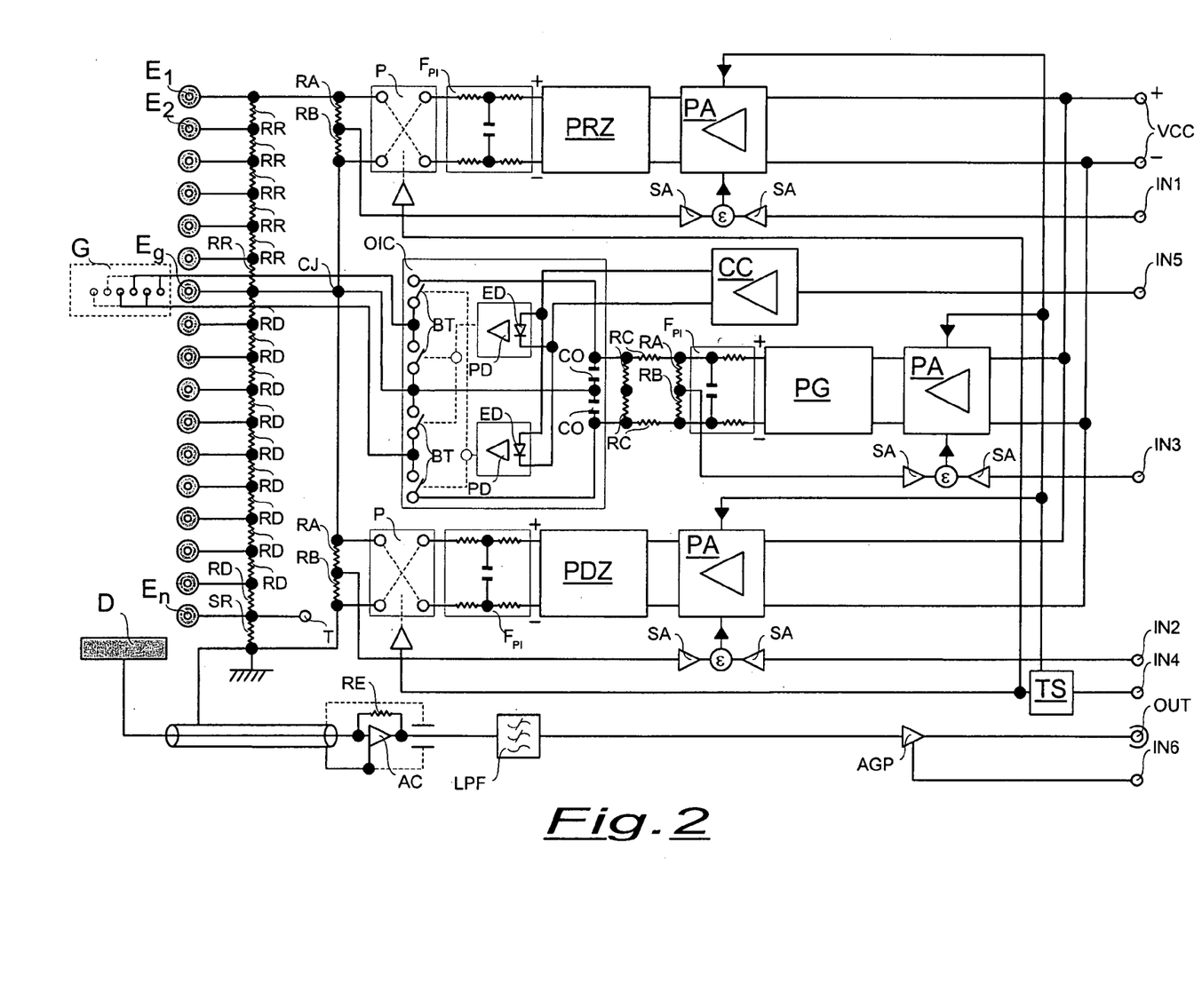
FIG. 2 is an electrical schematic of a control circuit for the IMS instrument of FIG. 1.

The realization of control circuits capable of generating a non-uniform field in the chamber of the instrument, and in particular the preferred condition of a field made of the sum of two uniform fields $E_{RZ}$ and $E_{DZ}$, different from each other, will be apparent to those skilled in the electrical arts. Only by way of example, a possible realization of such a control circuit is illustrated below with reference to FIG. 2. In FIG. 2, it is seen that the control circuit according to the present embodiment of the invention suitably comprises a high voltage power supply PRZ for the electrodes $E_1, E_2, \ldots, E_g$ arranged in the reaction zone RZ, a high voltage power supply PG for grid G and a high voltage power supply PDZ for the electrodes $E_g, E_{g+1}, \ldots, E_n$ arranged in the drift zone DZ. The power supplies PRZ, PG and PDZ are galvanically insulated, with the power supplies PRZ and PDZ connected in series and power supply PG symmetrically connected to a common junction point CJ connected to the electrode $E_g$ of grid G. The power supply PRZ supplies a continuous voltage variable from 0 to about 2000 V for powering a resistive divider comprising a series of resistors RR, for example with a resistance of 470 kilo-ohms (kΩ), which mutually connect two by two the adjacent electrodes $E_1, E_2, \ldots, E_g$ of the reaction zone RZ. The power supply PDZ, alike power supply PRZ, powers a resistive divider comprising a series of resistors RD, for example with a resistance of 470 kΩ, which mutually connect two by two the adjacent electrodes $E_g, E_{g+1}, \ldots, E_n$ of the drift zone DZ. The power supply PG, which generates a maximum voltage of 100 V, controls the positive and negative potential differences of the two alternated series of wires of grid G with respect to the potential of the grid electrode $E_g$.

Each of the power supplies PRZ, PG and PDZ comprises a voltage regulator, a high frequency oscillator, a voltage elevator transformer and a rectifier, so that they supply a continuous high voltage output linearly variable from 0 V to the maximum declared value, when they are powered by a continuous low voltage external source Vcc, for instance of 10 V. Input and output of the power supplies PRZ, PG and PDZ are insulated and galvanically separated from each other, thereby allowing the use of floating configurations with two or more modules connected in series. Although power supplies of this kind, according to the known art, offer a fair input/output conversion linearity and the high voltage potential is stable and smooth, for obtaining the extreme stability required for the use of the IMS instrument in the multi-component quantitative analysis, an external and separate negative feedback loop has been inserted for each single power supply in order to obtain a nearly perfect transfer linearity and a particular insensitivity to possible load changes. The residual ripple of the high voltage has been considerably reduced by adopting pi filters $F_{PI}$ connected to the outputs of the power supplies PRZ, PDZ and PG. The output voltage from the power supplies PRZ and PDZ is kept constant at the ends of the relevant resistive dividers comprising resistors RR and RD through auxiliary voltage dividers which are connected in parallel to them and comprise a pair of resistors RA, RB, for example, with a resistance of about 50 mega-ohms (MΩ) and about 50 KΩ, respectively. Also, the output voltage from the power supply PG is kept constant through an auxiliary voltage divider comprising a pair of resistors RA, RB, for example, with a resistance of 50 MΩ and 50 KΩ, respectively. The signals taken between resistors RA and RB of these dividers are compared in an analog way with control signals coming from terminals IN1, IN2 and IN3 which can be in turn connected to a programmable control unit (not shown in the figure) with microprocessor, for example, a computer of a known kind provided with suitable interfaces. The difference between these signals, i.e., the error signal, is amplified by signal amplifiers SA and through power amplifiers PA. The necessary supply voltage is generated for the oscillator/rectifier module of the power supplies PRZ, PG and PDZ, so as to cancel said difference through a negative feedback. Since the loop gain of the feedback system is very high, in particular greater than 100,000, the output voltage from the power supplies PRZ, PG and PDZ is linearly proportional to the control signals provided by the control unit through terminals IN1, IN2 and IN3, as well as is independent from load and power fluctuations, if any. The maximum current which can be supplied by each power supply PRZ and PDZ is about 1.5 milliamperes (mA), while PG can supply up to 30 mA. The power supply PG of the control grid G comprises a further fixed divider comprising four resistors RC, for example with a resistance of about 50 kΩ, which provides for supplying a symmetrical differential voltage for powering the switching circuit of grid G. The power supplies PRZ and PDZ are mutually connected in series and both generate, in a totally independent manner, a voltage variable from 0 to about 2000 V, thereby allowing to apply to the whole system of electrodes $E_i$ of chamber C a total voltage variable from 0 to about 4000 V but with the possibility of controlling in an independent manner the potential of the electrodes $E_1, E_2, \ldots, E_g$ of the reaction zone RZ and the potential of the electrodes $E_g, E_{g+1}, \ldots, E_n$ of the drift zone DZ. The polarity of the potential generated by the power supplies PRZ and PDZ can be inverted through a signal coming from the control unit through a terminal IN4. The polarity inversion of the output voltage of each power supply is obtained by using controlled switches P comprising four highly insulated reed relays which are mounted according to a bridge scheme and are controlled by a known time switch TS. Due to the undefined and different switching time of each relay, the high voltage is completely disconnected during the switching step in order to avoid that, while two relays arranged on contiguous lines of the bridge are simultaneously closed, a power supply or the resistive divider connected thereto could undergo a temporary short circuit. For this purpose, when the polarity inversion signal is received from terminal IN4, the time switch TS temporarily inhibits the working of the power amplifiers PA and automatically restores their state only after that all the relays of switches P have actually switched and that the fluctuations of their contacts have faded. The polarity inversion occurs simultaneously and in the same direction for the power supplies PRZ and PDZ. The power supply PG used for powering grid G is not involved with the polarity inversion but its working is inhibited anyway for safety during the switchings. The average time for the polarity inversion is about 1 second (s) against a relay switching time of about 30 milliseconds (ms).

The resistive dividers powering electrodes $E_i$ and made up of resistors RR and RD mutually connected in series, are terminated toward the "cold" side, grounded, by a shunt resistor SR, having a resistance negligible with respect to the resistance of resistors RR and RD, for instance 10 kΩ, at the ends of which a terminal T is arranged, from which a signal proportional to the current crossing the same dividers can be taken. During normal working conditions, the current of the dividers, once the voltages of the power supplies PRZ and PDZ have been fixed, will be constant since the current absorbed by electrodes $E_i$ can be considered negligible. However, if a working anomaly would occur, due for example to a jump spark between one or more electrodes inside chamber C, the current absorbed by the relevant electrodes would considerably increase and the variation could be detected at terminal T.

The potential of electrode $E_g$ of grid G is the one present at the summing node of the two power supplies PRZ and PDZ and changes with the value set for these latter. Grid G is driven with a potential pulse which is symmetric with respect to the summing node and has a relatively low value, for example from about 10 to 20 V, obtained through the power supply PG. Since the summing node may have potentials variable with respect to 0 V up to a maximum of about 2000 V, positive or negative, it is necessary to use an opto-isolated circuit OIC for controlling the potential of the members of grid G. Circuit OIC comprises four complementary bipolar transistors BT with a high switching speed which act as switches and are base-driven by two pairs of photodiodes PD. Two pairs of emitter diodes ED, connected to a logic control circuit CC of a known type suitable for sending a control pulse, induce the photodiodes PD to conduct in alternated pairs in reply to the same pulse. Circuit OIC not only carries out the necessary optical de-coupling between the high voltage components ("warm" side) and the grounded ones ("cold" side), but also provides for control pulses with a high switching speed, however, without requiring an active powering in the "warm" side. The photocurrent generated by photodiodes PD directly drives the bases of transistors BT without the intervention of other active devices.

Since the potential pulse supplied to grid G is symmetric with respect to the junction point of the two power supplies PRZ and PDZ, the polarity inversion is not necessary for the power supply PG, which therefore always works with a fixed polarity. In the known instruments, the grid voltage is usually controlled so as to be proportional to the electric field along the instrument axis, e.g., in a common instrument the grid voltage is such as to produce in the plane of grid G an electric field triple with respect to the one along axis x. In the instrument according to the present invention, it is instead possible to have electric fields $E_{RZ}$ higher than normal, for example for overcoming the above mentioned technical problem of the signal saturation. With a high field $E_{RZ}$ the ions in the reaction zone RZ are strongly accelerated and a portion thereof, even if small, could pass into the drift zone DZ also in "closed" grid conditions, thereby creating problems in the subsequent analysis. The possibility of controlling the grid voltage independently from the potentials of the two series of electrodes allows to avoid this technical problem.

The electric charges collected on the detecting electrode D must be properly amplified before they are sent to an analog-to-digital conversion and processing system. An operational device AC uses an operational device with a very low inner current lost, for instance lower than about 75 femto-amperes (fA), fed back in an inverting configuration with a resistor RE, for example with a resistance of about 1 giga-ohms (GΩ) and a sensitivity of 1 volt/nano-amperes (V/nA). The operational device is followed by a low noise amplifier with a fixed gain equal to 50 so as to obtain a current-to-voltage converter having a sensitivity equal to 20 pico-amperes/volt (pA/V). A passive low-pass filter LPF having a slope of about 12 desibels/octave (dB/octave) and a cutoff frequency of about 5 kilo-hertz (KHz) at −3 dB is connected to circuit AC acting as preamplifier and current-to-voltage converter. Filter LPF can cancel or attenuate all the spurious components of the signal of detector D without introducing significant distortions or attenuations of the usable signal. Device AC is in turn connected to an amplifier/attenuator stage AGP with a gain which is digitally programmable through a control signal coming from a terminal IN6. The aim of this amplifier is to optimize the level of the current signal before it reaches a terminal OUT for being connected to the input of an analog to digital (A/D) converter (not shown in the figure). Causing this A/D converter to work always close to its scale end value, for instance about 10 V, without however saturating it, the whole converter resolution, for example of 16 bit, can be exploited with any kind of signal. The gain of amplifier AGP can be programmed directly and in real time by the control unit by means of a 8-bit binary word which therefore allows to obtain 255 different amplification or attenuation values from 16 to 0.0625 with steps of 0.0625.

Figure 3:
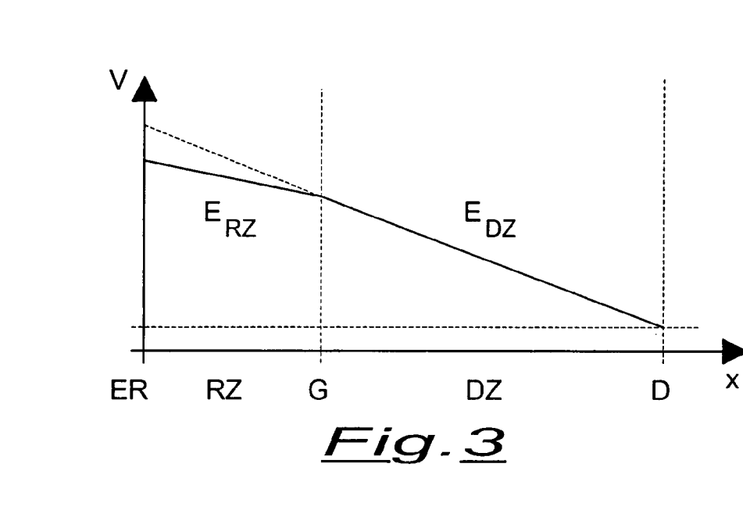
FIGS. 3 to 5 are graphs of the electric voltage trend along the longitudinal axis of the IMS instrument of FIG. 1.
Figure 4:
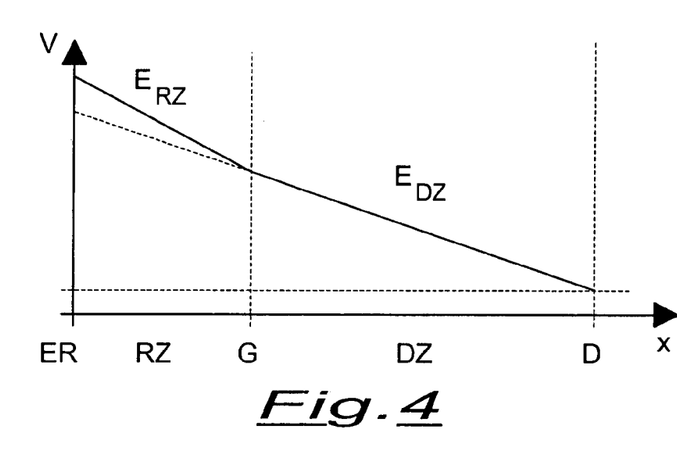
Figure 5:
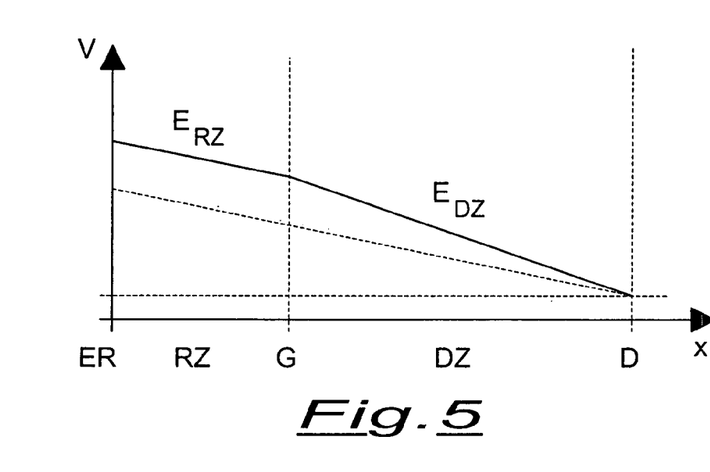

FIGS. 3 to 5 are graphs that show possible trends of the electric field in the chamber C of an IMS instrument of the invention; particularly, in these graphs it is represented the preferred condition in which a uniform electric field $E_{RZ}$ is present in the reaction zone RZ and a uniform electric field $E_{DZ}$, having an intensity different from the one in the reaction zone RZ, is present in the drift zone DZ. Both these two electric fields can be modified according to particular needs or problems met in an analysis.

This non-uniform field, made up by the sum of two different uniform fields, may be used in the method of the invention to resolve the problems previously described of IMS analyses. For example, when from a first preliminary analysis it is noted that the species $S_i$ cannot be seen or the concentrations of the same are such to reach the instrument saturation, the modification of the value of the electric field $E_{RZ}$ can be exploited for shifting the read range of the instrument toward the low or the high concentrations, respectively.

According to a first embodiment of the method of the invention, if the concentrations of the species $S_i$ are too low, the intensity of the electric field $E_{RZ}$ is decreased. This situation is shown in FIG. 3, wherein the abscissa axis represents the axis x of chamber C. The left end of the axis x corresponds to the position of electrode ER, the right vertical dotted line corresponds to the position of detector D and the middle vertical dotted line corresponds to the position of grid G dividing the instrument into the reaction zone RZ on the left and the drift zone DZ on the right. The ordinate axis represents the electric potential V. The horizontal dotted line represents the ground potential at which detector D is kept. The continuous segments in the graph represent the real electric potential, while the dotted segment in the RZ zone represents what would have been the electric field according to the prior art. The reduction of the intensity of the electric field $E_{RZ}$ as illustrated in FIG. 3 leads to a lower speed, and thus, to a longer residence time of ions in the reaction zone RZ with consequent increase of the advancement of the reaction of type I, i.e., with the formation of a greater quantity of ions $S_i^+$. The reduction of the electric field $E_{RZ}$ therefore allows to shift the lower sensitivity level of the instrument toward the low concentrations.

Alternately, if a saturation of the instrument signal is observed, the intensity of the field $E_{RZ}$ can be increased as shown in FIG. 4, wherein the symbols have the same meaning as in FIG. 3. In this second embodiment of the inventive method the opposite effect is obtained, i.e., the reduction of the residence time of ions in the reaction zone RZ and therefore of the advancement of the reaction of type I, thus decreasing the concentration of the ions $S_i^+$. Therefore, the same effect which is achieved in the traditional analyses with the dilution of the sample gas with a pure gas is obtained, but without the above cited complications for the dilution method. The increase of the electric field $E_{RZ}$ permits shifting the upper sensitivity limit of the instrument toward the high concentrations.

In a third embodiment of the method of the invention, the variation of the electric field $E_{DZ}$ can be exploited for improving the possibility of interpreting the spectrum with the peak deconvolution process. In the situation shown in FIG. 5, graphically analogous to FIGS. 3 and 4, a suitable increase of the intensity of the electric field $E_{DZ}$ and the consequent decrease of the residence time of the ions $S_i^+$ in this zone allow to reduce the quantity of ions $B_j^+$ generated by reactions of type III or IV, in which the additional gases $B_j$ present in this zone participate. Since the additional ions $B_j^+$ introduce in the final spectrum distortions which complicate or make impossible the determination of the area of the RIP and of the peaks generated by the ions $S_i^+$, a suitable increase of the electric field $E_{DZ}$ leads to the reduction of the phenomenon of the spectrum distortion and to a spectrum that is easier to interpret.

An increase of the intensity of the electric field $E_{DZ}$ and the consequent reduction of the residence time of the ions $S_i^+$ and $R^+$ in zone DZ further allows to minimize the quantity of charge exchanged by the ions $S_i^+$ and $R^+$ with the additional species $B_j$ in reactions of type I, III or IV, and therefore, to maximize the signal due to the species $S_i$ and R.

Preferably, the IMS instrument of the invention is connected to a suitable programmable control unit of a known kind with a microprocessor, for example, a computer provided with suitable interfaces. This unit processes in an automatic way and in real time the spectrum representing the primary result of the IMS analysis. As a result of this automatic analysis of the primary data, the control unit directly supplies to an operator the data relating to the concentration of the species $S_i$ (i=1, . . . , n) in the analyzed gas.

In all the method variations of the invention, the same unit which analyzes the primary data and supplies the concentration values of the species $S_i$ preferably also uses these data for automatically carrying out the continuous control of the analysis conditions, thereby continuously bringing, through a "feedback" mechanism, the electric fields $E_{RZ}$ or $E_{DZ}$ to optimal values for carrying out the analysis. In particular, the control unit checks that the peaks relating to the expected species $S_i$ are present and measurable, automatically decreasing in real time the intensity of $E_{RZ}$ in the contrary. The control circuit also checks the presence of the RIP, automatically increasing in real time the intensity of $E_{RZ}$ in the contrary. Finally, the control unit checks that the spectrum is not difficult to be interpreted due to an excessive height of the baseline or to peak overlappings, increasing the intensity of $E_{DZ}$ in the contrary.

The invention will be further disclosed by the following non-limiting examples. These examples show some embodiments intended to teach those skilled in the art how to put the invention into practice and to represent the best way considered for carrying out the invention. In all the following tests, both representing the method of the invention and comparative tests which do not represent the method, the flow of gaseous mixture coming into chamber C from duct IC is kept equal to about 0.5 liters per minute (lpm). The ionization of the sample is achieved by means of a ionizing member IM of $^{63}$Ni. The opening time of grid G is 200 microseconds (µs) in each test. Preliminary tests showed that in these conditions the typical flight times t of the species present in the tests are generally comprised between about 15 and 30 ms. The electric current c measured by detector D is expressed in arbitrary units (a.u.). For each peak in the graphs, it is indicated a "simplified" species, corresponding to the simplest ion even if the species actually present in the instrument are generally made up of these ions variously associated with neutral molecules.

EXAMPLE 1

This example represents the effect of the increase of the electric field $E_{RZ}$ in an analysis with several species in argon (Ar). The test employed argon (Ar) containing, as intentionally added impurities, 30 ppb of methane ($CH_4$) and 30 ppb of carbon dioxide ($CO_2$). During the test the presence of about 1.5 ppb of water ($H_2O$) in the analyzed gas was determined as background gas, released by the materials of the inner parts constituting the instrument. Pure argon (Ar) is employed as drift gas.

Figure 6:
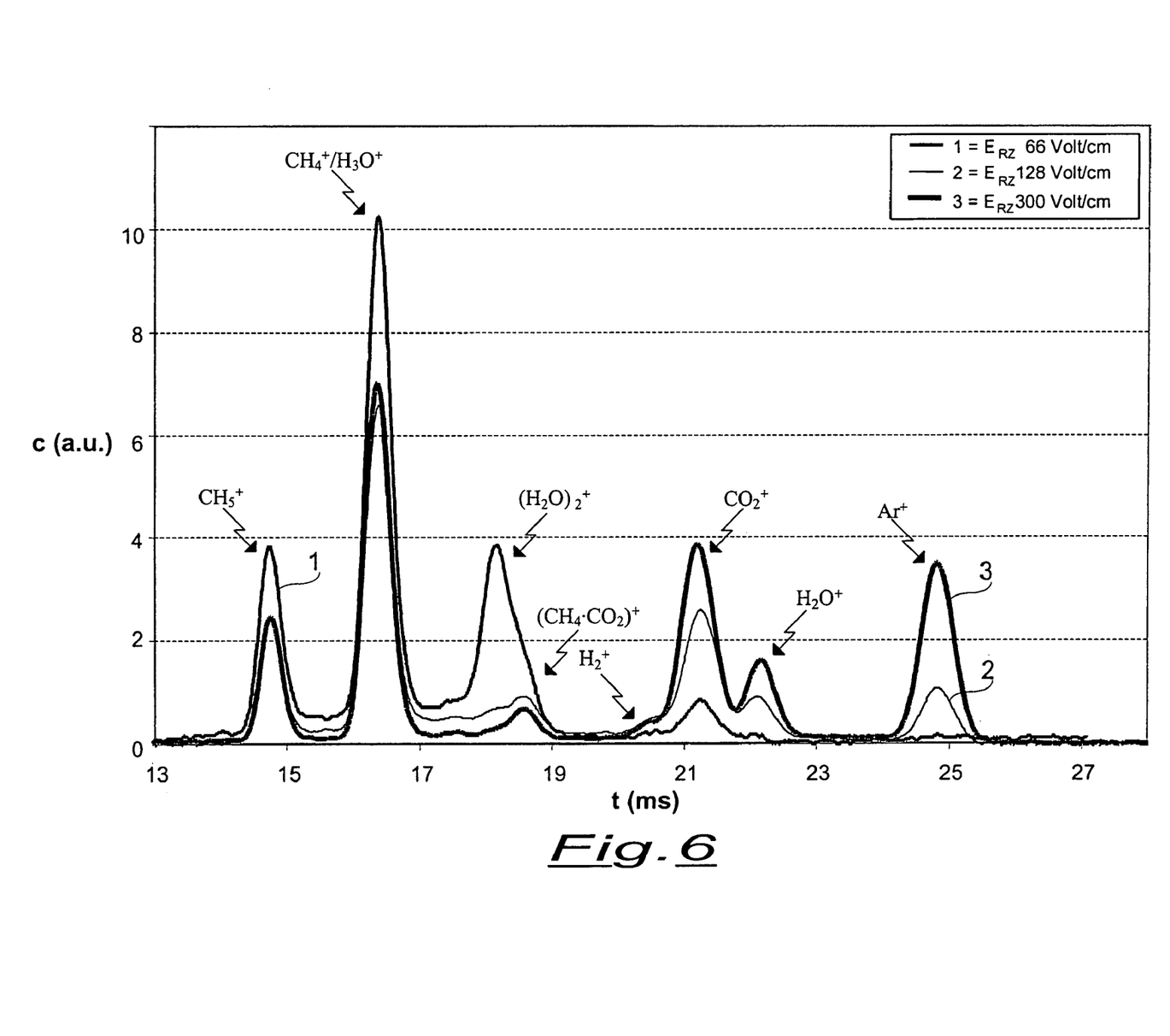
FIGS. 6 to 10 are graphs of spectra obtained in four examples of IMS analyses carried out by using the IMS instrument of FIG. 1.

The test is initially carried out in the conditions of the known art, that is by employing the instrument in uniform conditions of electric field, which has an intensity equal to about 66 volts per centimeter (V/cm) along the whole axis of the instrument. In a preliminary test without intentionally added impurities, it was determined that the peak of $Ar^+$ (the RIP in this case) was centered at about 25 ms in these conditions. In the analysis, the extinction of the RIP was observed. The result of this test is shown in FIG. 6 as curve 1. As previously explained, in these condition the quantitative analysis cannot carried out, and therefore, results that already with 30 ppb of $CH_4$ and 30 ppb of $CO_2$ the instrument reaches the signal saturation. The test is then repeated twice, by setting the electric field $E_{RZ}$ first to 128 V/cm and then to 300 V/cm, leaving instead the electric field $E_{DZ}$ in the drift zone DZ at 66 V/cm. The results of these tests are shown in FIG. 6 as curves 2 and 3, respectively. By increasing $E_{RZ}$, the value of the RIP monotonically increases, and that already with a field $E_{RZ}$ of 128 V/cm the analysis can be carried out. The trend of other peaks in the spectrum is not monotonic with respect to field $E_{RZ}$. By increasing $E_{RZ}$, the peaks corresponding to the analyzed species should decrease, but this does not happen for the peaks relating to the ions $CO_2^+$ and $H_2O^+$ centered around about 21 and 22 ms, respectively. The reason is that these ions are reactant ions in secondary reactions, for example, of the kind $CO_2^+ + CH_4 \rightarrow (CO_2.CH_4)^+$, and therefore, their concentration increases when the residence time in the reaction zone RZ which is inversely proportional to the intensity of field $E_{RZ}$ decreases.

The result of this test confirms that the increase of $E_{RZ}$ allows to shift the read range of a IMS instrument toward the high concentrations.

EXAMPLE 2

Figure 7:
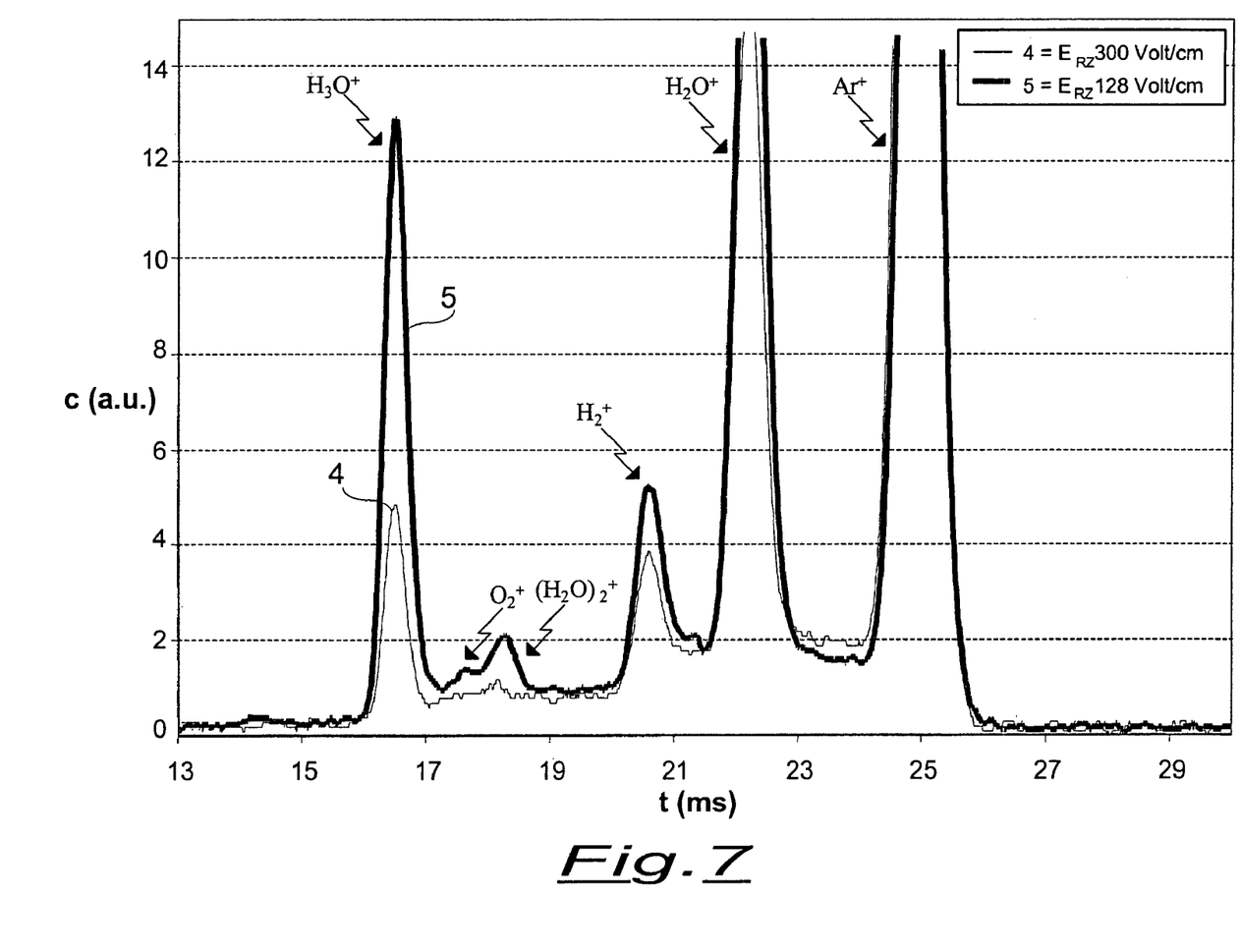

This example represents the effect of the decrease of the electric field $E_{RZ}$ in an analysis of oxygen in argon ($Ar^+$ is the RIP). Pure argon (Ar), intentionally added with 0.05 ppb of oxygen, is employed as sample gas. During the analysis, the gas is added with water which is released by the inner parts of the instrument and generates different species detected in the spectrum. From a preliminary test with a higher concentration of oxygen it is known that this species generates an ion $O_2^+$ which has a drift time of about 17.5 ms. The analysis is first performed with an intensity of the electric field $E_{RZ}$ equal to 300 V/cm. The result of this test is shown in FIG. 7 as curve 4, and does not show the presence of the oxygen peak. The test is then repeated with a value of field $E_{RZ}$ equal to 128 V/cm, while leaving unchanged the field value in the drift zone at 300 V/cm. The result is shown in FIG. 7 as curve 5, and in this case the oxygen peak can be detected in a way sufficient for calculating its concentration.

The result of this test confirms that the decrease of $E_{RZ}$ allows to shift the read range of a IMS instrument toward the low concentrations.

EXAMPLE 3

Figure 8:
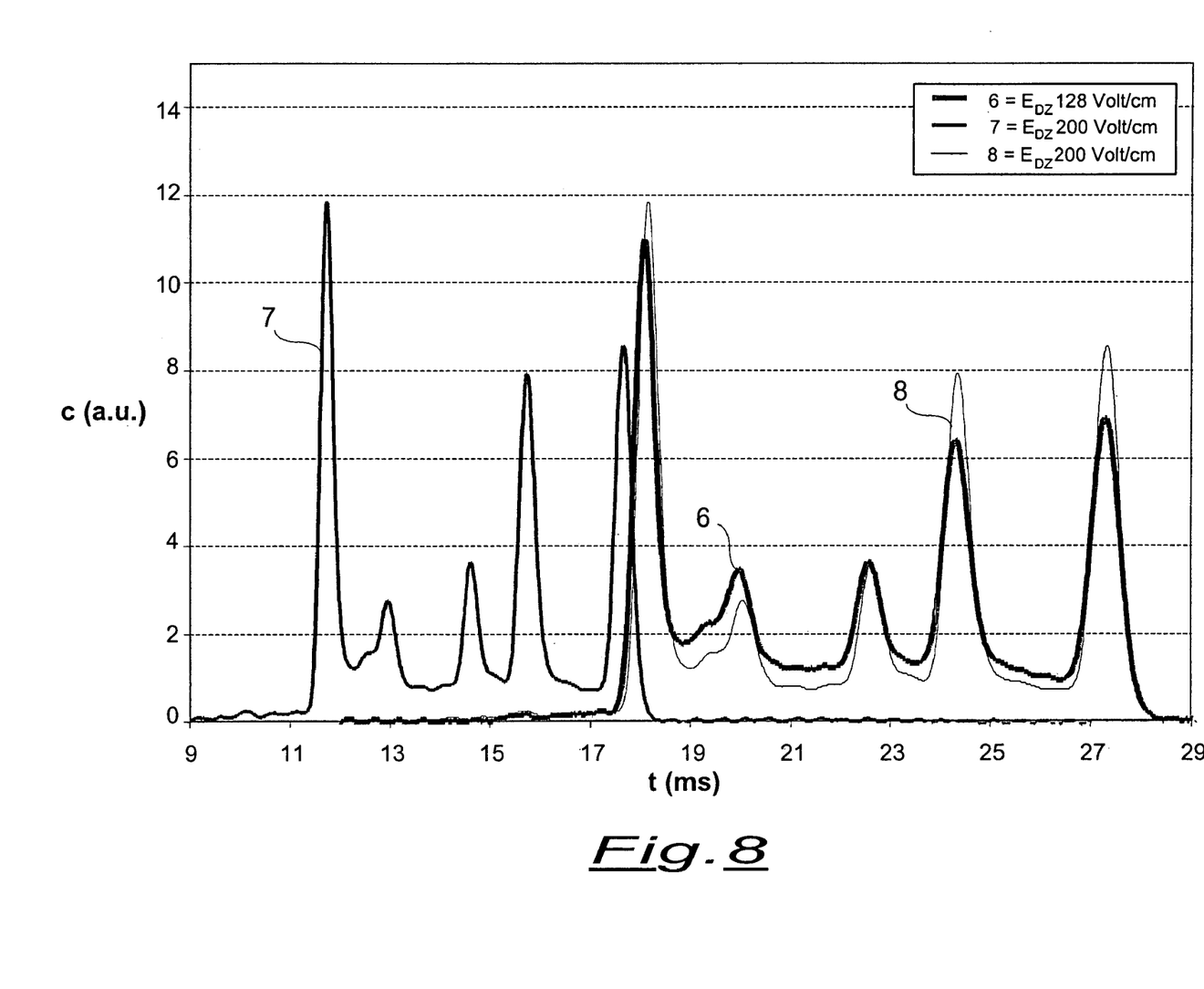

This example represents the effect of the change of the electric field EDZ. The sample gas is argon ($Ar^+$ is the RIP) without intentionally added impurities, thus containing only hydrogen and water released by the inner parts of the instrument. A first test is performed with a value of the field uniform in the whole instrument and equal to 128 V/cm. The result of this test is shown in FIG. 8 as curve 6. The test is repeated while keeping the value of the electric field $E_{RZ}$ at 128 V/cm, but increasing the value of $E_{DZ}$ to 200 V/cm. The result of this test is shown in FIG. 8 as curve 7. Obviously, the increase of the electric field $E_{DZ}$ causes the reduction by a scale factor of all the drift times, thereby "contracting" the spectrum toward the short flight times. For completely appreciating the effect of the modification of $E_{DZ}$ on the spectrum shape, curve 7 should be suitably "rescaled," thus taking each peak back to the correspondent drift times of curve 6. This operation is simply carried out by the control unit by determining the ratio between the drift times of ion $Ar^+$ in the two spectra and by multiplying the drift times of curve 7 by this ratio. Curve 8 is the result of this operation: as it can be seen in the Fig., the increase of $E_{DZ}$ has the effect of lowering the height of the bottom line between the peaks, and of better defining the shape of these latter, lifting their height and reducing the width at the base. The spectrum of curve 8 allows a better deconvolution of the peaks, and therefore, an easier determination of the kind and the concentration of the species present in the analyzed gas.

EXAMPLE 4

Figure 9:
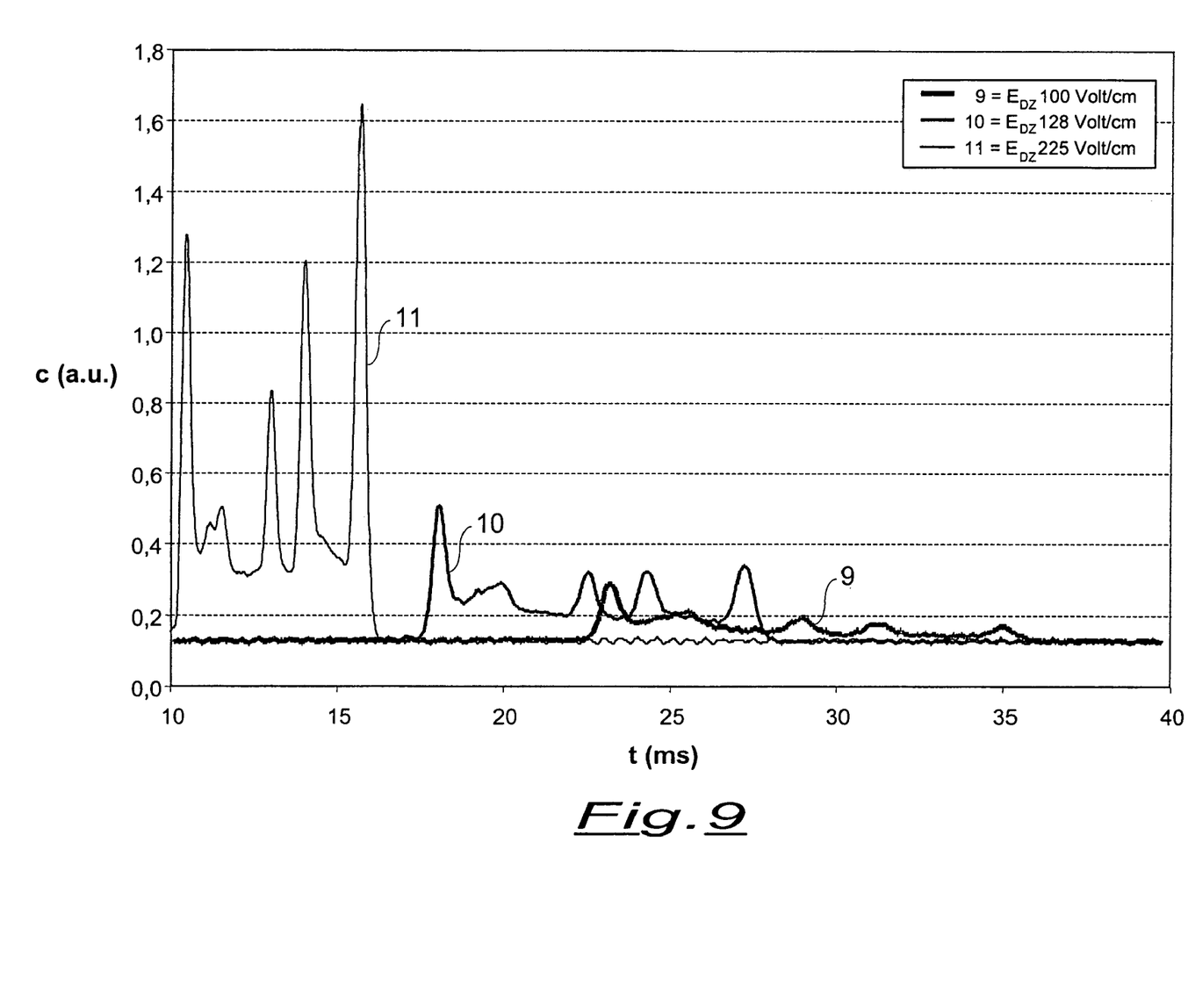
Figure 10:
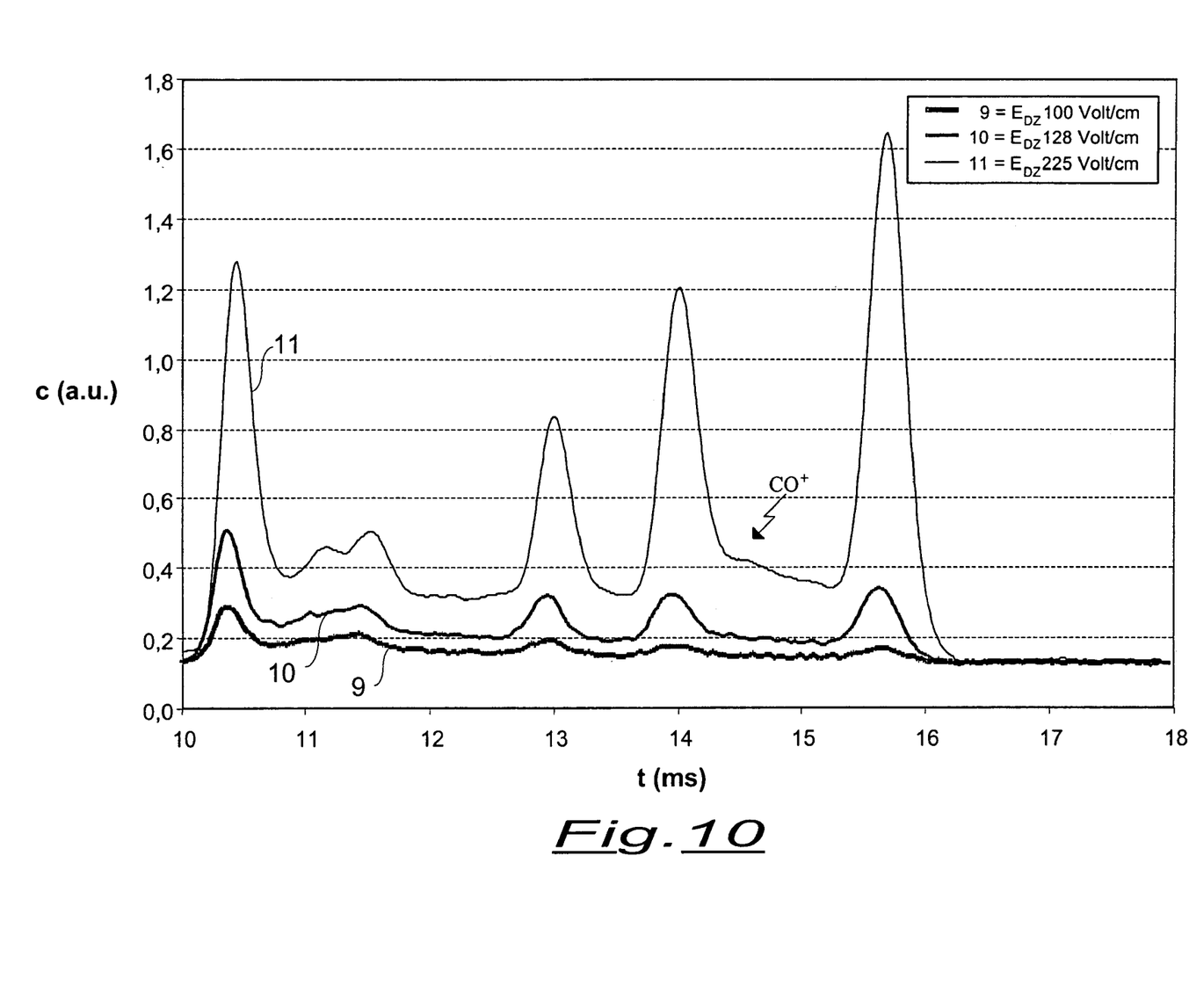

This example represents the effect of the change of the electric field $E_{DZ}$. The test employed argon ($Ar^+$ is the RIP) containing, as intentionally added impurities, 1.1 ppb of oxygen ($O_2$), 0.5 ppb of carbon monoxide (CO) and 0.3 ppb of carbon dioxide ($CO_2$). During the test the presence of about 0.8 ppb of water ($H_2O$) and about 2.4 ppb of hydrogen ($H_2$) was determined in the analyzed gas as background gas, released by the materials constituting the instrument. Pure argon (Ar) is employed as drift gas. A first test is performed with a field value uniform in the whole instrument and equal to 100 V/cm. The result of this test is shown in FIG. 9 as curve 9. The test is repeated while keeping the value of field $E_{RZ}$ at 100 V/cm, but increasing the value of $E_{DZ}$ to 128 V/cm. The result of this test is shown in FIG. 9 as curve 10. As observed in the discussion of example 3, the increase of the field in the drift zone DZ "contracts" the spectrum toward the short flight times. The test is repeated again while keeping the value of field $E_{RZ}$ at 100 V/cm but increasing the value of field $E_{DZ}$ to 225 V/cm. The result of this test is shown in FIG. 9 as curve 11. For better comparing curves 9, 10 and 11, curves 10 and 11 are "rescaled" as described in the discussion of example 3 and as shown in FIG. 10 together with curve 9 (left unchanged). The progressive increase of $E_{DZ}$ proportionally reduces the residence time of the ions in the drift zone DZ and thus limits the progress level of the reaction involving ion $CO^+$ and the background species $H_2O$ and $H_2$. This is clearly visible in FIG. 10, by noticing that the peak relating to ion $CO^+$ can be distinguished with increasing clarity when the intensity of field $E_{DZ}$ increases, i.e., while passing from curve 9 to curve 11.

The result of this test confirms that an increase of $E_{DZ}$, with the same $E_{RZ}$, allows to optimize the resolution of the IMS instrument, and thus to detect more easily and certainly the presence of impurities and to calculate more accurately their concentrations.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for carrying out analyses of a gas comprising one or more species by using an ion mobility spectrometer including a plurality of electrodes arranged in a chamber divided by an electrifiable grid into a reaction zone provided with an inlet for the gas to be analyzed and a drift zone provided with at least one ion detector, the method comprising:

the electrodes generating an electric field in the drift zone which has an intensity different from the electric field generated in the reaction zone and the electric fields are uniform in a space along the longitudinal axis of the chamber in each of the reaction and the drift zones and when the concentration of at least one species is higher than the upper read limit of the spectrometer, the intensity of the electric field in the reaction zone is increased.

2. A method for carrying out analyses of a gas comprising one or more species by using an ion mobility spectrometer including a plurality of electrodes arranged in a chamber divided by an electrifiable grid into a reaction zone provided with an inlet for the gas to be analyzed and a drift zone provided with at least one ion detector, the method comprising:

the electrodes generating an electric field in the drift zone which has an intensity different from the electric field generated in the reaction zone and the electric fields are uniform in a space along the longitudinal axis of the chamber in each of the reaction and the drift zones and when the concentration of at least one species is lower than the lower read limit of the spectrometer, the intensity of the electric field in the reaction zone is decreased.

3. A method for carrying out analyses of a gas comprising one or more species by using an ion mobility spectrometer including a plurality of electrodes arranged in a chamber divided by an electrifiable grid into a reaction zone provided with an inlet for the gas to be analyzed and a drift zone provided with at least one ion detector, the method comprising:

the electrodes generating an electric field in the drift zone which has an intensity different from the electric field generated in the reaction zone and the electric fields are uniform in a space along the longitudinal axis of the chamber in each of the reaction and the drift zones and when the spectrum resulting from a preliminary analysis is of difficult interpretation due to partial peak overlappings, a high baseline or the presence of peaks due to interaction of the ions with the background species, the intensity of the electric field in the drift zone is increased.

4. The method according to claim 1, wherein concentration conditions of at least one species are one of higher than the upper read limit of the instrument and lower than the lower read limit of the instrument or a condition when spectrum interpretation is difficult are checked by a programmable control unit with microprocessor, which according to these checks modifies in an automatic way and in real time the values of one of the intensity of the electric field in the reaction zone and the intensity of the electric field in the drift zone.

5. An instrument that carries out ion mobility spectrometric analyses of a gas comprising one or more species, the instrument comprising:
  a plurality of electrodes arranged in a chamber divided by an electrifiable grid into a reaction zone provided with an inlet for the gas to be analyzed and a drift zone provided with at least one ion detector;
  at least one control circuit for varying the potential of the electrodes so as to generate an electric field that is non-uniform along an axis which crosses the chamber, the control circuit being configured to set the electrodes in the reaction zone and the electrodes in the drift zone at potentials generating two uniform electric fields with different intensities inside the reaction and drift zones along the longitudinal axis of the chamber, the control circuit comprises a high voltage power supply for the electrodes in the reaction zone and a high voltage power supply for the electrodes in the drift zone, the power supplies being galvanically insulated and connected in series to a common junction point connected to the electrode closest to the grid; and
  wherein the power supplies are connected to resistive dividers comprising series of resistors which mutually connect two by two the electrodes of the reaction zone and of the drift zone.

6. The instrument according to claim 5, wherein the resistive dividers are grounded by a shunt resistor, at the ends of which a terminal is arranged for taking a signal proportional to the current crossing the same dividers.

7. The instrument according to claim 5, wherein the control circuit is configured to control the potential of the grid independently from the potential of the electrodes.

8. The instrument according to claim 7, wherein said means for controlling the potential of the grid comprise a high voltage power supply which is symmetrically connected to a common junction point connected to the electrode being the closest to the grid, which controls the positive and negative potential differences of two alternated series of members of the grid with respect to the potential of this electrode.

9. The instrument according to claim 8, wherein the power supply is connected to a voltage divider comprising four resistors, which supplies a symmetric differential voltage for powering the two alternated series of members of the grid.

10. The instrument according to claim 8, wherein the power supply is connected to the members of the grid through an opto-insulated circuit.

11. The instrument according to claim 10, wherein the opto-insulated circuit comprises four complementary bipolar transistors with a high switching speed which are base-driven by two pairs of photodiodes, in turn controlled by two pairs of emitter diodes connected to a logic control circuit suitable for sending a control pulse for inducing the photodiodes to conduct in alternated pairs in reply to the same pulse.

12. The instrument according to claim 5, wherein at least one of the power supplies comprises a voltage regulator, a high frequency oscillator, a voltage elevator transformer and a rectifier, so as to output a continuous voltage linearly variable from zero to a maximum value when they are powered by a continuous voltage external source.

13. The instrument according to claim 5, wherein the output of at least one of the power supplies is connected to pi filters.

14. The instrument according to claim 5, wherein the output of at least one of the power supplies is connected to auxiliary voltage dividers comprising a pair of resistors, wherein the signal taken between these resistors are compared in an analog way with control signals coming from terminals connectable to external control units, while the difference between these signals is amplified by signal amplifiers, so as to generate, by means of power amplifiers, a voltage for powering the power supplies, thereby canceling the difference through a negative feedback.

15. The instrument according to claim 5, wherein the control circuit is configured to invert the polarity of the potential generated by at least one of the power supplies according to a signal coming from a terminal.

16. The instrument according to claim 15, wherein the control circuit includes controlled switches for inverting the polarity comprising four highly insulated reed relays which are mounted according to a bridge scheme and are controlled by a time switch.

17. The instrument according to claim 16, wherein the time switch is connected to the power amplifiers arranged upstream of at least one of the power supplies, so as to deactivate them when the polarity is inverted.

18. The instrument according to claim 5, wherein the ion detector is connected to an output through a charge amplifier provided with an operational device with a very low inner current lost, fed back in an inverting configuration with a resistor.

19. The instrument according to claim 18, wherein the amplifier is followed by a low noise amplifier with a fixed gain so as to obtain a current-to-voltage converter.

20. The instrument according to claim 18, wherein the amplifier is connected to a low-pass filter suitable for canceling or attenuating all the spurious components of the signal of the ion detector.

21. The instrument according to claims 18, wherein the amplifier is connected to an amplifier/attenuator stage with a gain programmable in a digital manner through a control signal coming from a terminal.

* * * * *